(12) United States Patent
Husmark et al.

(10) Patent No.: US 9,283,297 B2
(45) Date of Patent: Mar. 15, 2016

(54) SANITARY ARTICLE COMPRISING A MICROBE-INHIBITING COMPOSITION

(75) Inventors: Ulrika Husmark, Mölnlycke (SE); Ulla Forsgren Brusk, Pixbo (SE)

(73) Assignee: SCA HYGIENE PRODUCTS AB, Göteborg (DE)

( * ) Notice: Subject to any disclaimer, the term of this patent is extended or adjusted under 35 U.S.C. 154(b) by 490 days.

(21) Appl. No.: 12/514,909

(22) PCT Filed: Nov. 17, 2006

(86) PCT No.: PCT/SE2006/001313
§ 371 (c)(1),
(2), (4) Date: May 14, 2009

(87) PCT Pub. No.: WO2008/060200
PCT Pub. Date: May 22, 2008

(65) Prior Publication Data
US 2010/0030172 A1    Feb. 4, 2010

(51) Int. Cl.
| A61F 13/15 | (2006.01) |
|---|---|
| A61L 15/36 | (2006.01) |
| A61F 13/47 | (2006.01) |
| A61L 15/20 | (2006.01) |

(52) U.S. Cl.
CPC .............. *A61L 15/36* (2013.01); *A61F 13/15* (2013.01); *A61F 13/47* (2013.01); *A61L 15/20* (2013.01)

(58) Field of Classification Search
CPC ............ A61F 13/511; A61F 13/51113; A61F 13/51108; A61F 13/8405; A61K 35/66; A61K 35/74; A61K 35/741; A61K 35/744; A61L 15/20; A61L 15/22; A61L 15/36
USPC .................................... 604/359, 360
See application file for complete search history.

(56) References Cited

U.S. PATENT DOCUMENTS

| 5,134,229 A * | 7/1992 | Saferstein ............... A61L 15/28 424/443 |
|---|---|---|
| 5,762,948 A | 6/1998 | Blackburn et al. |
| 6,110,908 A | 8/2000 | Guthery |

(Continued)

FOREIGN PATENT DOCUMENTS

| CN | 1787841 A | 6/2006 |
|---|---|---|
| EP | 1 060 240 B1 | 12/2000 |

(Continued)

OTHER PUBLICATIONS

Falagas et al., "Probiotics for Prevention of Recurrent Vulvovaginal Candidiasis a Review" Journal of Antimicrobial Chemotherapy, 2006, vol. 58, pp. 266-272.

(Continued)

*Primary Examiner* — Melanie Hand
(74) *Attorney, Agent, or Firm* — Buchanan Ingersoll & Rooney PC

(57) ABSTRACT

A sanitary article (1) such as a sanitary napkin, a panty liner, an incontinence protector, a diaper, an incontinence pad, a feminine insert, a tampon, or the like includes a top sheet (2) and a microbe-inhibiting composition (8). The microbe-inhibiting composition (8) includes at least one extracellular product of at least one probiotic bacterium and/or at least one probiotic bacterium and at least one additive in the form of an organic acid, with at least one of its pKa value not exceeding 5.5, and/or a salt thereof.

17 Claims, 7 Drawing Sheets

(56) References Cited

U.S. PATENT DOCUMENTS

| | | | |
|---|---|---|---|
| 6,277,374 | B1 | 8/2001 | Vandenbergh et al. |
| 6,531,126 | B2 | 3/2003 | Farmer |
| 6,716,435 | B1 | 4/2004 | Farmer et al. |
| 6,761,885 | B1 | 7/2004 | Hakansson et al. |
| 7,482,023 | B2 | 1/2009 | Runeman et al. |
| 2001/0033838 | A1 | 10/2001 | Farmer |
| 2002/0044926 | A1 | 4/2002 | Reid et al. |
| 2002/0090365 | A1 | 7/2002 | Chrisope |
| 2003/0143262 | A1 | 7/2003 | Brusk et al. |
| 2004/0142832 | A1 | 7/2004 | Runeman et al. |
| 2004/0241151 | A1 | 12/2004 | Husmark et al. |
| 2004/0243076 | A1 | 12/2004 | Husmark et al. |
| 2004/0253217 | A1 | 12/2004 | Samuelsson et al. |
| 2005/0176613 | A1 | 8/2005 | Wai Cheung et al. |
| 2005/0276836 | A1 | 12/2005 | Wilson et al. |
| 2006/0062774 | A1 | 3/2006 | Davis et al. |
| 2006/0171936 | A1 | 8/2006 | Gueniche et al. |
| 2006/0177429 | A1 | 8/2006 | Farmer et al. |
| 2008/0193428 | A1 | 8/2008 | Zhou et al. |
| 2010/0040673 | A1 | 2/2010 | Husmark et al. |
| 2010/0069860 | A1 | 3/2010 | Forsgren Brusk et al. |
| 2010/0136210 | A1 | 6/2010 | Forsgren-Brusk et al. |

FOREIGN PATENT DOCUMENTS

| | | | | |
|---|---|---|---|---|
| EP | 1 140 226 | B1 | 10/2001 | |
| GB | 2 112 285 | A | 7/1983 | |
| RU | 2212902 | C2 | 9/2003 | |
| WO | WO 92/13577 | A1 | 8/1992 | |
| WO | WO 94/23585 | A1 | 10/1994 | |
| WO | WO 97/02846 | A1 | 1/1997 | |
| WO | WO 98/46261 | | 10/1998 | |
| WO | WO 99/17788 | A1 | 4/1999 | |
| WO | WO 99/17813 | A1 | 4/1999 | |
| WO | WO 99/45099 | A1 | 9/1999 | |
| WO | WO 99/45976 | A1 | 9/1999 | |
| WO | WO 00/35502 | A1 | 6/2000 | |
| WO | WO 00/61201 | A1 | 10/2000 | |
| WO | WO 0061201 | A1 * | 10/2000 | ............ A13L 15/36 |
| WO | WO 00/76878 | A1 | 12/2000 | |
| WO | WO 02/28446 | A1 | 4/2002 | |
| WO | WO 03/038068 | | 5/2003 | |
| WO | WO 2004/022727 | | 3/2004 | |
| WO | WO 2004/060416 | A1 | 7/2004 | |
| WO | WO 2004/101008 | A1 | 11/2004 | |
| WO | WO 2004105822 | A1 * | 12/2004 | ........... A61K 35/744 |
| WO | WO 2005/034970 | A1 | 4/2005 | |
| WO | WO 2005/086870 | A2 | 9/2005 | |
| WO | WO 2006/114061 | A1 | 11/2006 | |
| WO | WO 2008/060199 | A1 | 5/2008 | |
| WO | WO 2008/060200 | A1 | 5/2008 | |

OTHER PUBLICATIONS

Hooton et al., "*Escherichia* Coil Bacteriuria and Contraceptive Method" JAMA, 1991, vol. 265, No. 1, pp. 64-69.
Osset et al., "Papel de Lactobacillus como foctor Protector de la Candidiasis Vaginal" Med Clin (Barc), 2001, vol. 117, pp. 285-288.
Redondo-Lopez et al., "Emerging Role of Lactobacilli in the Control and Maintenance of the Vaginal Bacterial Microflora" Reviews of Infectious Diseases, 1990, vol. 12, No. 5, pp. 856-872.
Strus et al., "Dzialanie In Vitro Bakterii Z Rodzaju Lactobacillus Izolowanych Z Pochwy Na Grzybywywolujace Kandydoze Sromu I Pochwy" Med. Dotw. Mikrobiol., 2005, vol. 57, pp. 7-17, in Russian with English Abstract.
Rönnqvist, "Inhibition of *Candida albicans* and *Candida glabrata* by two Lactobacillus Fermentum Strains" Essum AB, 2008, 11 pages.
Brusk et al., U.S. Appl. No. 12/515,252, entitle "New Agent" filed May 15, 2009.
International Search Report and the Written Opinion of the International Search Authority Forms (PCT/ISA/210 and PCT/ISA/237) issued in corresponding International Application No. PCT/SE2006/001311 dated Jul. 6, 2007.

Notification of Receipt of Record Copy Form (PCT/IB/301) issued in corresponding International Application No. PCT/SE2006/001311 dated Dec. 14, 2006.
International Search Report and the Written Opinion of the International Searching Authority Forms (PCT/ISA/210 and PCT/ISA/237) issued in corresponding International Application No. PCT/SE2006/001312 dated Jul. 5, 2007.
U.S. Appl. No. 12/515,252, Brusk et al.
Written Opinion of the International Preliminary Examining Authority Form (PCT/IPEA/408) issued in corresponding International Application No. PCT/SE2006/001312 dated Jan. 27, 2009.
L. Beuchat, "Comparison of Anti-*Vibro* Activities of Potassium Sorbate, Sodium Benzoate, and Glycerol and Sucrose Esters of Fatty Acids," *Applied and Environmental Microbiology*, Jun. 1980, pp. 1178-1182, vol. 39, No. 6.
D. Rönnqvist et al., "*Lactobacillus fermentum* Ess-1 with unique growth inhibition of vulvo-vaginal candidiasis pathogens" *Journal of Medical Microbiology*, 2007, pp. 1500-1504, vol. 56.
D. Rönnqvist et al. "Selection and characterization of a *Lactobacillus plantarum* strain promising as a urogenital probiotic," *Microbial Ecology in Health and Disease*, 2005, pp. 75-82, vol. 17.
Maidak et al., "A New Version of the RDP (Ribosomal Database Project)" Nucleic Acids Research, 1999, vol. 27, No. 1, pp. 171-173.
Rainey et al., "The Genus *Nocardiopsis* Represents a Phylogenetically Coherent Taxon and a Distinct Actinomycete Lineage: Proposal of *Nocardiopsaceae* fam. nov." International Journal of Systematic Bacteriology, 1996, vol. 46, No. 4, pp. 1088-1092.
Copending Application, U.S. Appl. No. 12/514,851, filed May 14, 2009 by Ulrika Husmark et al.
Form PCT/ISA/210 dated Jun. 29, 2007.
Form PCT/ISA/237 dated Jun. 29, 2007.
Form PCT/IPEA/408 dated Jan. 27, 2009.
G. B. Hill et al, "Bacteriology if the Vagina", Duke University Medical Center, Departments of Obstetrics & Gynecology and Microbiology, Durham, North Carolina and Department of Obstetrics & Gynecology and Department of Medicine, University of Washington, pp. 23-29, Seattle Washington, USA.
B. Runeman et al., "Experimental *Cadidia albicans* Lesions in Healthy Humans: Dependence of Skin pH", Investigative Report, Acta Derm Venereal, 2000, vol. 80, pp. 421-424, Department of Dermatology, Sahlgrenska University Hospital, Goteborg, Sweden.
Russian Federation Office Action dated Apr. 27, 2010 in counterpart foreign Application No. 2009122992/15(031913); and translation thereof.
Official Action issued on Jun. 10, 2011 by the Chinese Patent Office in corresponding Chinese Patent Application No. 200680056412.0, and partial English language translation of the Official Action.
Cabo, M.L., et al., "Apparent Antifungal Activity of Several Lactic Acid Bacteria against *Penicillium discolor* is Due to Acetic Acid in the Medium," *Journal of Food Protection*, 2002, pp. 1309-1316, vol. 65, No. 8, International Association for Food Production, Des Moines, IA, USA.
Corsetti, A., et al., "Antimould activity of sourdough lactic acid bacteria: identification of a mixture of organic acids produced by *Lactobacillus sanfrancisco* CB1," *Appl Microbial Biotechnol*, 1998, pp. 253-256, vol. 50, Springer-Verlag, Berlin, Heidelberg, DE.
De Man, J. C., et al., "A Medium for the Cultivation of Lactobacilli," *Journal of Applied Bacteriology*, 1960, pp. 130-135, vol. 23, No. 1, Society for Applied Bacteriology, Blackwell Scientific Publications Ltd., Oxford, England.
Heriban, V., et al., "Process and metabolic characteristics of *Bacillus coagulans* as a lactic acid producer," *Letters in Applied Microbiology*, 1993, pp. 243-246, vol. 16, John Wiley & Sons, Wiley Online Library.
Lee, Ki-Yong, et al., "Thin layer chromatographic determination of organic acids for rapid identification of bifidobacteria at genus level," *Journal of Microbiological Methods*, 2001, pp. 1-6, vol. 45, Elsevier Science B.V.; The Netherlands.
Mishra, Charumati, et al., "Production of anti-microbial substances by probiotics," *Asia Pacific J ain Nutr*, 1996; pp. 20-24, vol. 5, No. 1, John Wiley & Sons, Wiley Online Library.

(56) References Cited

OTHER PUBLICATIONS

Moon, Nancy J., et al., "Inhibition of the growth of acid tolerant yeasts their synergistic mixtures," *Journal of Applied Bacteriology*, 1983, pp. 453-460, vol. 55, Issue 3, John Wiley & Sons, Inc., Wiley Online Library.

Narendranath, NV, et al., "Effects of acetic acid and lactic acid on the growth of *Saccharomyces cerevisiae* in a minimal medium," *Journal of Industrial Microbiology & Biotechnology*, 2001, pp. 171-177, vol. 36, Nature Publishing Group, www.nature.com, Springer, Berlin, Heidelberg, DE.

Silva, M., et al., "Antimicrobial Substance from a Human *Lactobacillus* Strain," *Antimicrobial Agents and Chemotherapy*, Aug. 1987, pp. 1231-1233, vol. 31, No. 8, American Society for Microbiology, USA.

Stiles, J., et al., "Antifungal Activity of Sodium Acetate and *Lactobacillus rhamnosus*," *Journal of Food Protection*, 2002, pp. 1188-1191, vol. 65, No. 7, International Association for Food Protection, Des Moines, IA, USA.

\* cited by examiner

SANITARY ARTICLE COMPRISING A MICROBE-INHIBITING COMPOSITION

TECHNICAL FIELD

The present invention relates to a sanitary article, such as sanitary napkins, panty liners, incontinence protectors, diapers, tampons, or the like, that comprises an extracellular product of at least one probiotic bacterium and/or at least one probiotic bacterium and at least one of the selected additive giving a synergistic inhibitory effect on *Candida albicans* or other unwanted microorganisms.

BACKGROUND OF THE INVENTION

The urogenital area harbors a complex microbial ecosystem comprising more than 50 different bacterial species (Hill et al., Scand. J. Urol. Nephrol. 1984; 86 (suppl.) 23-29). The dominating species for fertile women in this area are lactic acid producing bacteria belonging to the genus *Lactobacillus*. These lactic acid producing members are important for retaining a healthy microbial flora in these areas, and act as probiotic bacteria with an antagonistic effect against pathogenic microbial species. Lactic acid producing bacteria inhibit growth and colonization by other microorganisms by occupying suitable niches for colonization, by forming biofilms and competing for available nutrients, thereby excluding colonization by harmful microorganisms. Also, the production of hydrogen peroxide, specific inhibiting substances, such as bacteriocines, and organic acids (including lactic acid and acetic acid) that lower the pH, inhibit the growth and colonization by other microorganisms.

The microbial ecosystem of a healthy individual can be disturbed by the use of antibiotics, during hormonal changes, such as during pregnancy or use of contraceptives with estrogen, during menstruation, after menopause, in people suffering from diabetes etc. Also, microorganisms may spread from the anus to the urogenital area, this result in a disturbance of the normal microbial flora and leaves the individual susceptible to microbial infections such as vaginitis, candida infections, urinary tract infections and skin infections. Microorganisms commonly associated with these kinds of infections belong to the genera *Escherichia, Enterococcus, Pseudomonas, Proteus, Klebsiella, Streptococcus, Staphylococcus, Gardnerella* and *Candida*. Women are at particular risk due to their shorter distance between the anus and the urogenital tract; specially at risk are young women, who not yet have a well developed microflora in the urogenital area and older women, who in most cases no longer have a protective flora.

Similarly to the urogenital area, the skin is colonized by an array of organisms, which forms its normal flora. The numbers and identity of the organisms vary between different skin sites. This, together with the skin's structural barrier, provides the host with an excellent defense against invading microbes. The number of bacteria on the skin varies from a few hundred per $cm^2$ on the arid surfaces of the forearm and back, to tens of thousands per $cm^2$ on the moist areas such as the axilla and groin. This normal flora plays an important role in preventing foreign organisms from colonizing the skin, but it too needs to be kept in check, in order to avoid skin infections.

*Staphylococcus aureus* is the most common cause of minor skin infections, such as boils or abscesses, as well as more serious post-operative wound infection. Treatment involves drainage and this is usually sufficient for minor lesions, but antibiotics may be given in addition when the infection is severe and the patient has fever.

Toxic shock syndrome is a systemic infection caused by *S. aureus* strains which produce toxic shock syndrome toxin. The disease came to prominence through its association with tampon use by healthy women, but it is not confined to women and can occur as a result of *S. aureus* infection at non-genital sites.

Other common skin infections are caused by *Streptococcus pyogenes* (group A streptococci). The organisms are acquired through contact with other people with infected skin lesions and may first colonize and multiply on normal skin prior to invasion through minor breaks of the epithelium and the development of lesions.

Treatment with penicillin or erythromycin may be necessary to combat the infection.

*Candida* likes skin sites which are moist and warm and also rapidly colonizes damaged skin. Hence, the relative dryness of most areas of skin prevents the growth of *Candida*, which therefore are found in low numbers on healthy skin. *Candida* also colonizes the oral and vaginal mucosa and over-growth may result in disease in these sites. *C. albicans* is associated with diaper dermatitis. A study has shown that *C. albicans* induced lesions are remarkably influenced by pH, a lower skin pH giving less lesions (B. Runeman, Acta Derm Venereol 2000; 80: 421-424).

One way to reduce the problems with the kind of infections described above is to have a good personal hygiene. However, excessive use of cleaning agents not only decreases the amount of harmful microbes, but can harm the beneficial microbial flora, again render it susceptible for pathogenic species to colonize and cause infections. Alternatively, administration of lactic acid producing bacteria to the urogenital area and the skin, in order to out-compete pathogenic species and facilitate reestablishment and maintenance of a beneficial microbial flora in these areas, has been found to be a successful means to treat and prevent microbial infections It has been suggested that lactic acid producing bacteria can be delivered via absorbent products, such as diapers, sanitary napkin, incontinence guards, panty liners and tampons, as described in, for example, WO 92/13577, WO 97/02846, WO 99/17813, WO 99/45099 and WO 00/35502.

Other ways of delivering the lactic acid producing bacteria have also been suggested, such as a hygiene tissue that allows both cleaning and caring of the skin and urogenital area and delivery of probiotic lactic acid producing bacteria, for example, WO 04/060416.

A major problem with providing products intended to be used for transfer of lactic acid producing bacteria, is that the bacteria have to retain viability during transport and storage of the products. Lactic acid producing bacteria rapidly lose viability under semi moist conditions, and it is therefore important that the bacteria are not exposed to moisture during storage. One way to partly overcome this problem in absorbent products provided with lactic acid producing bacteria has been to supply the products with the bacteria, drying said products to remove most of the moisture in them and providing the product in moisture impervious packages (WO99/17813).

WO 00/61201 discloses a sanitary product containing an effective amount of a viable, non-pathogenic, probiotic bacterium, such as *Bacillus coagulans*, or an extracellular product thereof.

EP 1140226 describes the combination of a pH regulating substance in the form of a partially neutralized superabsorbent material with lactic acid-producing bacteria.

In view of the prior art there is still a need for sanitary articles with an improved prebiotic and/or probiotic effect, which articles are easy to store and transport.

SUMMARY OF THE INVENTION

In view of this prior art it is an object of the present invention to provide a sanitary article comprising a microbe-inhibiting composition with an enhanced probiotic and/or prebiotic effect. It is also an object of the present invention that said sanitary article comprising a microbe-inhibiting composition is easily transported and stored without the microbe-inhibiting composition losing its micro-flora balancing and health promoting function.

The above defined problems are solved by the present invention by a sanitary article such as sanitary napkins, panty liners, incontinence protectors, diapers, tampons or the like comprising a microbe-inhibiting composition comprising an extracellular product of at least one probiotic bacterium and/or at least one probiotic bacterium and at least one additive, in the form of an organic acid, having a pKa value not exceeding 5.5, and/or a salt thereof, giving a synergistic probiotic and/or prebiotic effect.

In one aspect said pKa value does not exceed 5.

According to the present invention said microbe-inhibiting extracellular product is a supernatant obtained by filtration or centrifugation of a culture of a probiotic bacterium.

In one embodiment of the invention said microbe-inhibiting composition is substantially free from probiotic bacteria, preferably not present in an amount higher than 100 CFU/ml and more preferably not higher than 10 CFU/ml.

In another embodiment of the invention said microbe-inhibiting composition comprises at least one probiotic bacterium and at least one of said additives.

In a further embodiment of the invention said microbe-inhibiting composition comprises at least one probiotic bacterium, an extracellular product of at least one probiotic bacterium and at least one of said additives.

In one aspect of the invention the probiotic bacterium is a lactic acid producing bacterium.

In a further aspect of the invention the lactic acid producing bacterium is *Lactobacillus plantarum* LB 931. In one other aspect of the invention the lactic acid producing bacterium is *Lactobacillus fermentum* Ess-1. In a further aspect of the invention the lactic acid producing bacteria is a combination of *Lactobacillus plantarum* LB 931 and *Lactobacillus fermentum* Ess-1.

In one aspect of the invention said additive is chosen from acetic acid, propionic acid, lactic acid, ascorbic acid, phenylalanine, citric acid, butyric acid, valeric acid, capronic acid, succinic acid and/or a salt thereof. Preferably said additive is chosen from acetic acid, propionic acid, lactic acid, phenylalanine, citric acid or succinic acid, ascorbic acid, and/or a salt thereof. Most preferably said additive is chosen from ascorbic acid, acetic acid, propionic acid, succinic acid and/or a salt thereof.

In another aspect of the invention said salt is a sodium salt; preferably sodium propionate or sodium acetate.

Since the microbe inhibiting composition of the invention combining a probiotic bacterium and/or an extracellular product thereof and an additive gives an unexpected synergistic effect in inhibition of pathogenic microorganisms, a sanitary article according to the invention comprising this microbe inhibiting composition has an enhanced probiotic and/or prebiotic effect. In addition a sanitary article of the present invention is easy to transport and store without the microbe inhibiting composition losing its beneficial properties.

DESCRIPTION OF THE DRAWINGS

FIG. 4b is a cross sectional view through the sanitary article according to the line II-II in FIG. 4a.

FIG. 5b is a cross sectional view through the sanitary article according to the line II-II in FIG. 5a.

DEFINITIONS

Figure 1:
FIG. 1. shows the growth of *C. albicans* in extracellular product of LB 931 with addition (50 mM) of different acids/salts.

Probiotics/probiotic in the present context relates to live microorganisms that confer a health benefit when administered in adequate amounts to a host.

By "lactic acid producing bacteria" is a meant a bacterium producing lactic acid. Preferred lactic acid producing bacteria for the object of the present invention include bacteria from the genera *Lactobacillus*, *Lactococcus* and *Pediococcus*. Preferably the selected bacterium used is from the species *Lactococcus lactis*, *Lactobacillus fermentum*, *Lactobacillus rhamnosus*, *Lactobacillus acidophilus* or *Lactobacillus plantarum*. More preferably the bacterial strain is selected from *Lactobacillus plantarum* or *Lactobacillus fermentum*. Even more preferably the lactic acid producing bacterium is *Lactobacillus plantarum* LB 931 (deposition No. (DSMZ): DSM 11918) and *Lactobacillus fermentum* Ess-1, (deposition No. (DSMZ): DSM 17851).

Prebiotics/prebiotic in the present contexts relates to substances that promote a balanced micro flora when administered in adequate amounts to a host. Examples are nutrients for probiotic bacteria, substances that promote adhesion to the host for probiotic bacteria, pH-regulating substances and extracellular products from probiotic bacteria.

By microbe-inhibiting is meant the inhibition of growth, colonization and/or survival of other microorganisms.

By extracellular product is meant products secreted in cultures of probiotic bacteria which extracellular products have an antimicrobial effect. The extracellular product is obtained from the bacterial cell cultures by e.g. filtration, centrifugation, or both of these, and the resulting supernatant comprising the extracellular product possesses antimicrobial activity useful in a microbe-inhibiting composition.

The term "sanitary article" refers to products that are placed against the skin of the wearer to absorb and contain body exudates, like urine, faeces and menstrual fluid, which articles also can be used to deliver probiotic bacteria to these areas. The invention mainly refers to disposable sanitary articles, which means articles that are not intended to be laundered or otherwise restored or reused as a sanitary article after use. Examples of disposable sanitary articles include feminine hygiene products such as sanitary napkins, panty liners, sanitary panties, feminine inserts and tampons; diapers and pant diapers for infants and incontinent adults; incontinence pads; diaper inserts and the like.

DETAILED DESCRIPTION

The present invention pertains to solve the problem of growth, colonization and/or survival of pathogenic microorganisms in the urogenital area and/or in a sanitary article during use thereof.

This problem is in the present invention solved by applying an extracellular product of at least one probiotic bacterium and/or at least one probiotic bacterium and at least one additive, in the form an organic acid having a pKa value not exceeding 5.5 and/or a salt thereof, together forming a microbe-inhibiting composition, to a sanitary article.

It should be noted that of course a combination of two or more probiotic bacterial strains may be used to produce the extracellular product of the invention. Also, it is of course possible to use a combination of at least two probiotic bacterial strains in a microbe-inhibiting composition according to the present invention.

The prior art discloses sanitary articles only comprising probiotic bacteria or extracellular products thereof. However the microbe-inhibiting effect is not always completely satisfying and there are many problems to overcome when producing and storing sanitary articles containing viable microorganisms as previously discussed.

In the present invention it has been found that by adding an additive, in the form an organic acid having a pKa value not exceeding 5.5, preferable not exceeding 5, and/or a salt thereof, to a probiotic bacteria or extracellular products thereof, there is an surprisingly large increase in the inhibition of *Candida albicans* and several other micro-organisms such as for example *E. coli* and *S. Saprofyticus*.

The present invention in some embodiments also aims to decrease the problems with retaining the microbe-inhibiting effect of the sanitary article during storage. Since all the effect in some embodiments and at least parts of the effect in other embodiments comes from a composition comprising substantially no living organisms, the problem of keeping the micro-organisms viable and thus functional is eliminated or decreased.

Figure 4A:
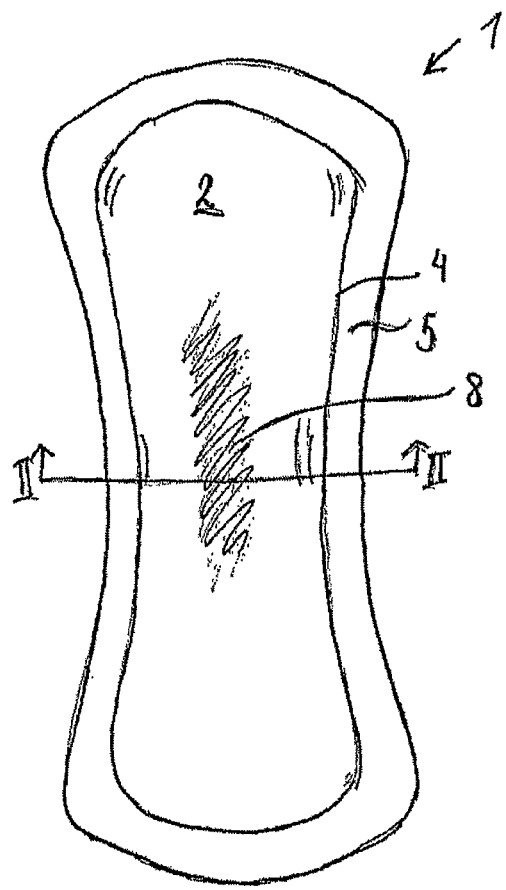
FIG. 4a is a plan view of a sanitary article according to the present invention.
Figure 4B:
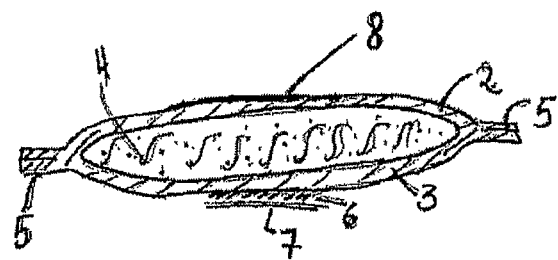
Figure 5A:
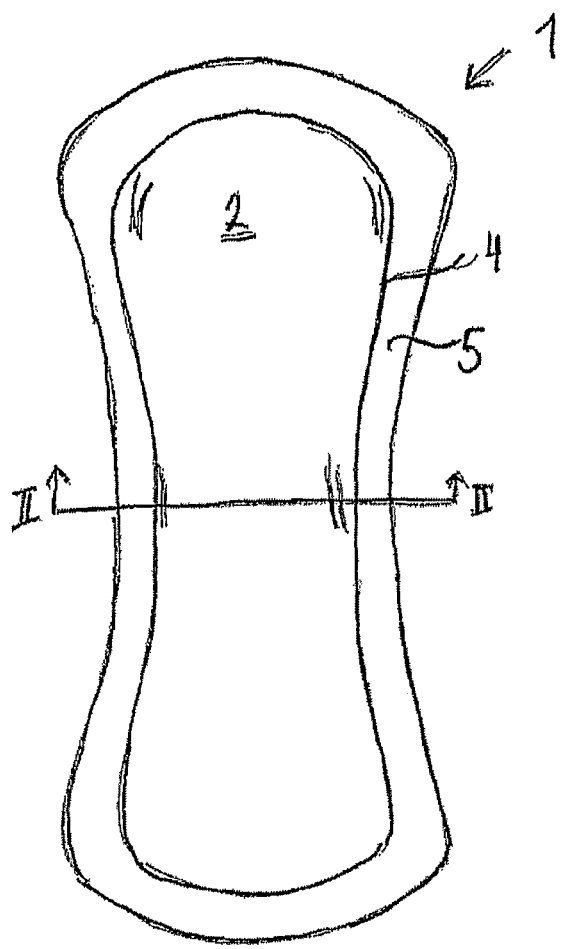
FIG. 5a is a plan view of a sanitary article according to the present invention.
Figure 5B:
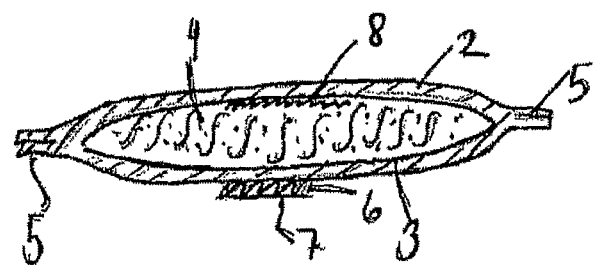

FIGS. 4 and 5 show an exemplary embodiment of a sanitary napkin 1 which comprises a liquid permeable topsheet 2, a backsheet 3 and an absorbent structure 4 enclosed there between. The liquid permeable topsheet 2 can be composed of a nonwoven material, e g spunbonded, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and be readily penetrated by body fluid, such as urine or menstrual fluid.

The backsheet 3 may consist of a thin plastic film, e.g. a polyethylene or polypropylene film, a nonwoven material coated with a liquid impervious material, a hydrophobic nonwoven material, which resists liquid penetration. Laminates of plastic films and nonwoven materials may also be used. The backsheet material is preferably breathable so as to allow vapour to escape from the absorbent structure, while still preventing liquids from passing through the backsheet material.

The topsheet 2 and the backsheet 3 have a somewhat greater extension in the plane than the absorbent structure 4 and extend out side the edges thereof to form projecting portions 5. The layers 2 and 3 are connected to each other within the projecting portions 5, e g by gluing or welding by heat or ultrasonic. The topsheet and/or the backsheet may further be attached to the absorbent structure by any method known in the art, such as adhesive or welding by heat or ultrasonic. The absorbent structure may also be unattached to the topsheet and/or the backsheet.

Fastening means in the form of a region 6 of an adhesive is provided on the side of the backsheet facing away from the wearer during use. The adhesive may releasably attach to the undergarment of the wearer. A release paper 7 protects the adhesive region 6 before use. The adhesive region 6 may have any suitable configuration, such as elongate or transverse strips, dots, full-coated areas etc.

In other embodiments (not illustrated) of sanitary articles according to the invention other types of fasteners, like friction fasteners, tape tabs or mechanical fasteners like hook-and-loop fasteners etc may be used to fasten the articles to the underwear or around the waist of the wearer. Some sanitary articles are in the form of pants and therefore do not need special fastening means. In other cases the sanitary article is worn in special elastic pants without the need for additional fasteners.

The absorbent structure 4 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent structure. It is also common to have absorbent structures comprising layers of different material with different properties with respect to liquid acquisition capacity, liquid distribution capacity and storage capacity. This is well-known to the person skilled in the art and does therefore not have to be described in detail. The thin absorbent bodies, which are common in today's sanitary articles, often comprise a compressed mixed or layered structure of cellulosic fluff pulp and superabsorbent. The size and absorbent capacity of the absorbent structure may be varied to be suited for different uses such as sanitary napkins, panty liners, adult incontinence pads and diapers, baby diapers, pant diapers, etc. In some cases the sanitary articles are in the form of a feminine insert or an incontinence insert with substantially no absorbing function at all, the main function for these article is instead to carry and possibly deliver a for example health promoting substance. Examples on inserts are a nonwoven layer, a perforated plastic film or a foam layer, or laminates thereof, all preferably with means for attachment to a garment. Said insert can optionally comprise a back sheet 3.

An object of the present invention is to provide sanitary articles, such as sanitary napkins, panty-liners, diapers, incontinence guards etc. suitable for absorbing bodily fluids and simultaneously release a microbe-inhibiting composition 8 that is to be transferred to the skin, or alternatively, in order to inhibit the growth of unwanted microorganisms in the sanitary article itself during use of the article.

It is understood that the sanitary article described above and shown in the drawings only represents non-limiting examples and that the present invention is not limited thereto, but can be used in any type of sanitary articles as defined above.

The probiotic bacteria which are suitable for use in the present invention produce in most cases acid and are in all cases non-pathogenic. There are many suitable bacteria identified herein below, although the invention is not limited to currently known bacterial species and strains as long as the above function and the objectives of the probiotic bacteria are fullfilled.

An important characteristic of the probiotic lactic acid producing bacteria is their capability to produce lactic acid and in some cases also other acids, said lactic acid increases the acidity of the skin mucosa which helps in preventing the growth, colonization and survival of undesired fungi and bacteria. Thus, by the mechanism of acid production, these probiotic bacteria inhibit the growth of competing and harmful bacteria and fungi. Further important characteristics of said bacteria is their ability to produce hydrogen peroxide and other microbe inhibiting substances and also their ability to adhere to cell surfaces and thereby prevent adhesion of other harmful bacteria and fungi to these surfaces.

Typical probiotic bacteria useful in a microbe-inhibiting composition of this invention are all members of the *Lactobacillus, Lactococcus* or *Pediococcus*, which are efficient lactic acid producers, and also including non-pathogenic members of the *Bacillus* genus, all members of the *Bifidobacterium* genus, and *Pseudomonas limbergii*, although certain species are especially preferred as described below.

Preferred members of the *Lactobacillus* genus include *Lactobacillus acidophilus, Lactobacillus bulgaricus, Lactobacillus casei, Lactobacillus cereale, Lactobacillus delbrukeii, Lactobacillus fermentum, Lactobacillus gaserii, Lactobacillus jensenii, Lactobacillus plantarum, Lactobacillus rhamnosus, Lactobacillus salivarius, Lactobacillus thermophilus, Lactobacillus paracasai sp. paracasai, Lactobacillus crispatus, Lactobacillus helveticus, Lactobacillus lactis*, and the like.

Particularly preferred is the novel bacterium *Lactobacillus fermentum* Ess-1 and *Lactobacillus plantarum* LB 931. LB 931 has previously been found valuable for preventing and/or treating urogenital infections as it inhibits growth of a large number of pathogenic microorganisms, in e.g. EP1060240. *Lactobacillus fermentum* Ess-1 (deposition No. (DSMZ): DSM 17851) was deposited according to the Budapest Treaty at Deutsche Sammlung von Mikroorganismen und Zellkulturen GmbH (Mascheroder Weg 1b, D-38124 Braunschweig) (depositor Essum AB, Box 3160, SE 90304 Umeå, Sweden, deposited on Jan. 6, 2006).

It should be noted that although in the examples below where only two Lactobacilli strains have been used, these bacterial strains should only be seen as a model for probiotic bacteria useful in the practice of the present invention. Therefore the below examples should not be seen as limiting for the present invention. It is intended that any probiotic bacteria may be used in the composition.

In one embodiment of the present invention when the microbe-inhibiting composition comprises an extracellular product and at least one of said additives, said composition is substantially free from probiotic bacteria. It is noted that it is extremely difficult to manufacture a composition that is totally free from probiotic bacteria, therefore the probiotic bacteria is preferably not present in the microbe-inhibiting composition in an amount higher than 100 CFU/ml and more preferably not higher than 10 CFU/ml. This composition has the advantage of less stringent storage requirements since the extracellular product is more durable than the live microorganism.

The extracellular product of the present invention is obtained from a bacterial culture. Bacteria suitable for the present invention secrete products having antimicrobial activity which is useful for the objectives of the present invention. In order to obtain the extracellular products, cell cultures are harvested as described below and the supernatant is obtained by centrifugation or filtration or both. The thus obtained supernatant has a microbe inhibiting activity due to the extracellular products comprised therein. An example of how the extracellular product may be prepared is described under Example 3.

The extracellular product may be in the form as when obtained directly from a bacterial culture but it is also possible to concentrate and/or purify the supernatant further. By purification is meant that some of the microbe-inhibiting substances are isolated by for example chromatography, crystallisation or distillation and used separately or in combination with other isolated substances.

The additive which is added to the probiotic bacteria and/or to the extracellular product in the present invention is in the form of an organic acid or a salt thereof. When choosing said additive this should of course be made from a product safety point of view. The organic acids or the corresponding salts should be of such nature that when applying them onto a sanitary article they should not cause any skin irritation to the wearer of the sanitary article, therefore the pKa of the organic acid, when the measurement are performed in water at 25° C., should preferably not be lower than 2. If the pKa values instead are too high, the organic ac ids or the salts thereof will mainly be in their acid forms. This means that the additive will not be sufficiently dissociated into a hydrogen ion and its deprotonated, anionic form, which is believed to be a prerequisite in order to obtain said synergistic microbe-inhibiting effect with the probiotic bacteria and/or the extracellular product thereof. Therefore the pKa value for the organic acid suitable for the present invention should be lower than 5.5, preferably lower than 5. If the organic acid suitable for the present invention have more than one pKa value, at least one of these values should be lower than 5.5, preferably lower than 5.

When the extracellular product is in the form of a supernatant, the solubility of these organic acids and/or the corresponding salts should be sufficiently high so that said additive can be dissolved in the supernatant. Alternatively, when the additive is in a dry/dried form on the sanitary article the solubility of the additive should be of such nature that the additive rapidly comes into solution when contacted by the bodily fluids during use of the sanitary article.

In a preferred embodiment of the present invention the additive is chosen from acetic acid, propionic acid, lactic acid, ascorbic acid, phenylalanine, citric acid, butyric acid, valeric acid, capronic acid, succinic acid and/or a salt thereof. Preferably said additive is chosen from acetic acid, propionic acid, lactic acid, ascorbic acid, phenylalanine, citric acid or succinic acid, and/or a salt thereof. Most preferably said additive is chosen from ascorbic acid, acetic acid, propionic acid, succinic acid and/or a salt thereof.

In one embodiment of the invention the salt is a sodium salt. Especially preferred salts are sodium propionate and sodium acetate.

When a sanitary article of the present invention comprises probiotic bacteria these are typically provided in amounts of about $10^6$-$10^{11}$ CFU of viable probiotic bacteria per article. Typically the bacteria are in the form of cells or spores which are provided in a suspension which is applied to the sanitary article which is thereafter dried. Preferably, the sanitary article will comprise about $10^8$-$10^{10}$ CFU per sanitary article, although these amounts may vary depending on the specific application, product formulation and intended use.

If the sanitary article instead of probiotic bacteria comprises the extracellular product, the sanitary article typically comprises about 0.5-100 ml and preferably comprises 1-10 ml of the extracellular product.

In combination with the extracellular product said additive is typically added with a concentration of 5-100 mM. When combined only with the probiotic bacteria said additive is typically added in amounts of 0.15 mg-2.6 g and preferably 0.3 mg-0.3 g to the sanitary article, although these amounts may vary depending on the specific application, product formulation and intended use.

The microbe-inhibiting composition may be directly applied to the sanitary article according to the invention or provided in a pharmaceutically acceptable carrier which enhances the transfer of the microbe-inhibiting composition, examples of such includes sticky agents such as petrolatum, an oil or a wax.

In one preferred embodiment the microbe inhibiting composition is in the form of a suspension, said suspension may be applied directly to the sanitary article by impregnation, spraying, printing or the like, whereafter the sanitary product is dried, by for e.g. heat drying.

In another preferred embodiment the microbe-inhibiting composition is in the form of a powder. The powder may be mixed into a pharmaceutically acceptable carrier as described above or be directly applied to the sanitary article as a powder, in this latter case preferably to the absorbent structure or between the absorbent structure and the top sheet, as illustrated in FIG. 5. In the case where the powder is mixed with a pharmaceutically acceptable carrier, this mixture may be applied to the sanitary article by impregnation, spraying, printing or the like, whereafter the sanitary article may be dried. A delivery device, meaning a separate pocket, possibly moisture impervious, attached to the top sheet of the sanitary article is also an advantageous way of deliver said microbe-inhibiting composition.

The powder according to the above may be obtained by evaporating the above discussed suspension such as by heat drying, convective drying, spray drying, freeze drying, or the like. It may be necessary to further mould the dried microbe-inhibiting composition in order to obtain a fine powder. The probiotic bacteria are preferably freeze dried.

The microbe inhibiting composition may be placed anywhere on the sanitary article as long as it comes in contact with the user of the sanitary article when in use. The microbe inhibiting composition 8 is preferably located on the top sheet of the sanitary article as shown in FIG. 4.

In an alternative preferred embodiment, shown in FIG. 5, the microbe inhibiting composition 8 is located between the top sheet 2 and the absorbent structure 4.

When the sanitary article comprises live probiotic bacteria the bacteria must be protected from moisture. The sanitary article may therefore be hermetically enclosed in a moisture-impervious package. WO 00/76878 gives an example of such a moisture impervious package. Another example of how the bacteria can be protected is by the use of a delivery system as exemplified in for example WO 02/28446.

A further possibility is to deliver said microbe-inhibiting composition separately in a form which is convenient to apply directly to an absorbent article by the user, for example in its liquid form, as a powder, dispersed in a lotion, dispersed in oil. The means for applying said microbe-inhibiting composition could be a spray, a roll-on device, a tube, a bottle, an ampull, a strip or a stick.

In a still further aspect of the invention the microbe-inhibiting composition is used in combination with the sanitary article according to the invention.

Another aspect of the invention is to preparing a sanitary article comprising applying said microbe-inhibiting composition to said sanitary article.

Experimental Section
Test 1

The purpose of this test was to determine whether selected additives affect the growth of *Candida albicans* and if an improved growth inhibition can be achieved when they are added to the extracellular products of *Lactobacillus plantarum*, LB 931. The additives used in this test were ascorbic acid, citric acid, phenylalanine, acetic acid, propionic acid and sodium propionate.

Method
Yeast Strain

A clinical isolate of *Candida albicans* (designated *C. albicans* 702) was used as test strain. It was isolated from the vagina of a woman with vaginal candidiasis.

Control

As control pure dMRSs broth (MRS broth without addition of sodium acetate) was used. A specified volume was transferred to wells of a micro titre plate and was let to air dry (45° C. minimum of 20 hrs).

Extracellular Product (ECP)

Cultures of LB 931 grown in dMRSs broth were centrifuged to pellet the cells and sterile filtered using a 0.22 μm filter (Millipore filter, Bedford, USA) in order to obtain the LB 931 supernatant comprising the LB 931 extracellular product. A specified volume of sterile filtered supernatant was transferred to wells of a micro titre plate and was let to air dry (45° C. minimum of 20 hrs) and thereafter resuspended in sterile distilled water to a concentration three times higher and 200 μl were transferred to 96-wells micro titre plates.

Extracellular Product with Additive

The additives were added to a final concentration of 50 mM to tubes containing the sterile filtered supernatant of LB 931. A specified volume was transferred to wells of a micro titre plate and was let to air dry (45° C. minimum of 20 hrs) and thereafter resuspended in sterile distilled water to a concentration three times higher (i.e. the volume of the sterile distilled water is about one third of the specified volume before air drying) and 200 μl were transferred to 96-wells micro titre plates.

Broth with Additive

The additives were added to a final concentration of 50 mM in dMRSs broth. pH was adjusted to the same pH-value as in the extracellular product with additive for the respective additive. A specified volume was transferred to wells of a micro titre plate and was let to air dry (45° C. minimum of 20 hrs) and thereafter resuspended in sterile distilled water to a concentration three times higher and 200 μl was transferred to 96-wells micro titre plates.

*Candida* was added to a final concentration of ~$10^4$ cells per well and the micro titre plate was incubated at 37° C. for 24 hrs.

pH for the different additives varied between 3.4±0.2. The pH for broth with additive and extracellular product with additive was always the same.

The test was blinded so that there could be no preconceived opinions colouring the results. The inhibition of *Candida* was evaluated and graduated, by two persons using a template, on a scale from five to zero based on visual observations of turbidity with a calculated mean value being presented. Wells containing strong growth of *Candida* in pure dMRSs-broth was graduated as five, while wells with no visual growth were graduated as zero.

Results

As can be seen in FIG. 1 very few additives themselves proved to have an effect on the growth of *Candida* although the pH was very low. The extracellular product of LB 931 was effective in the inhibition of *Candida*. This effect was surprisingly enhanced by the addition of the additives to the extracellular products of LB 931. For all additives in combination with the extracellular product of LB931, a very good growth inhibiting effect was achieved. The best effect was achieved when propionic acid was added to the extracellular product of LB931 (no growth at all).

Test 2

The purpose of these tests was to determine whether selected additives affect the growth of bacteria and if an improved growth inhibition can be achieved when they are added to the extracellular products of *Lactobacillus plantarum*, LB 931. The additives used in this test were sodium acetate, succinic acid, sodium propionate, acetic acid.

Method

Bacterial Strains

Clinical isolates of *E. coli* (designated *E. coli* 1) and *Staphylococcus saprophyticus* (*S. saprophyticus* 1) were used as test strains. They were isolated from the genital tract in women with urinary tract infections.

Control

As a control pure dM17s broth (M17 broth modified by addition of $MnSO_4$ (final conc. 0.04 g/l), $MgSO_4$ (final conc. 0.2 g/l) and glucose (final conc. 20 g/l) was used. 200 µl was added to 96-wells micro titre plates.

Extracellular Product (ECP)

Cultures of LB 931 grown in dM17s broth were centrifuged to pellet the cells and sterile filtered using a 0.22 µm filter (Millipore filter, Bedford, USA) in order to obtain the LB 931 supernatant comprising the LB 931 extracellular product. 200 µl were transferred to 96-wells micro titre plates.

Extracellular Product with Additive

The additives were added to a final concentration of 50 mM to tubes containing the sterile filtered suspension of LB 931. 200 µl was transferred to 96-wells micro titre plates.

Broth with Additive

The additives were added to a final concentration of 50 mM in dM17s broth. 200 µl were added to 96-wells micro titre plates.

10 µl of an over-night culture of *E. coli* resp. *S. saprophyticus*, both diluted 100×, were added to the wells in the micro titre plate which was incubated in 37° C. over night.

pH was adjusted to 6.9 in all trials.

The test was blinded so that there could be no preconceived opinions colouring the results. The inhibition of *E. coli* resp. *S. saprophyticus* was evaluated and graduated, by two persons using a template, on a scale from five to zero based on visual observations of turbidity with a calculated mean value being presented. Wells containing strong growth of *E. coli* resp. *S. saprophyticus* in pure dM17s-broth was graduated as five, while wells with no visual growth were graduated as zero.

Results

Figure 2A:
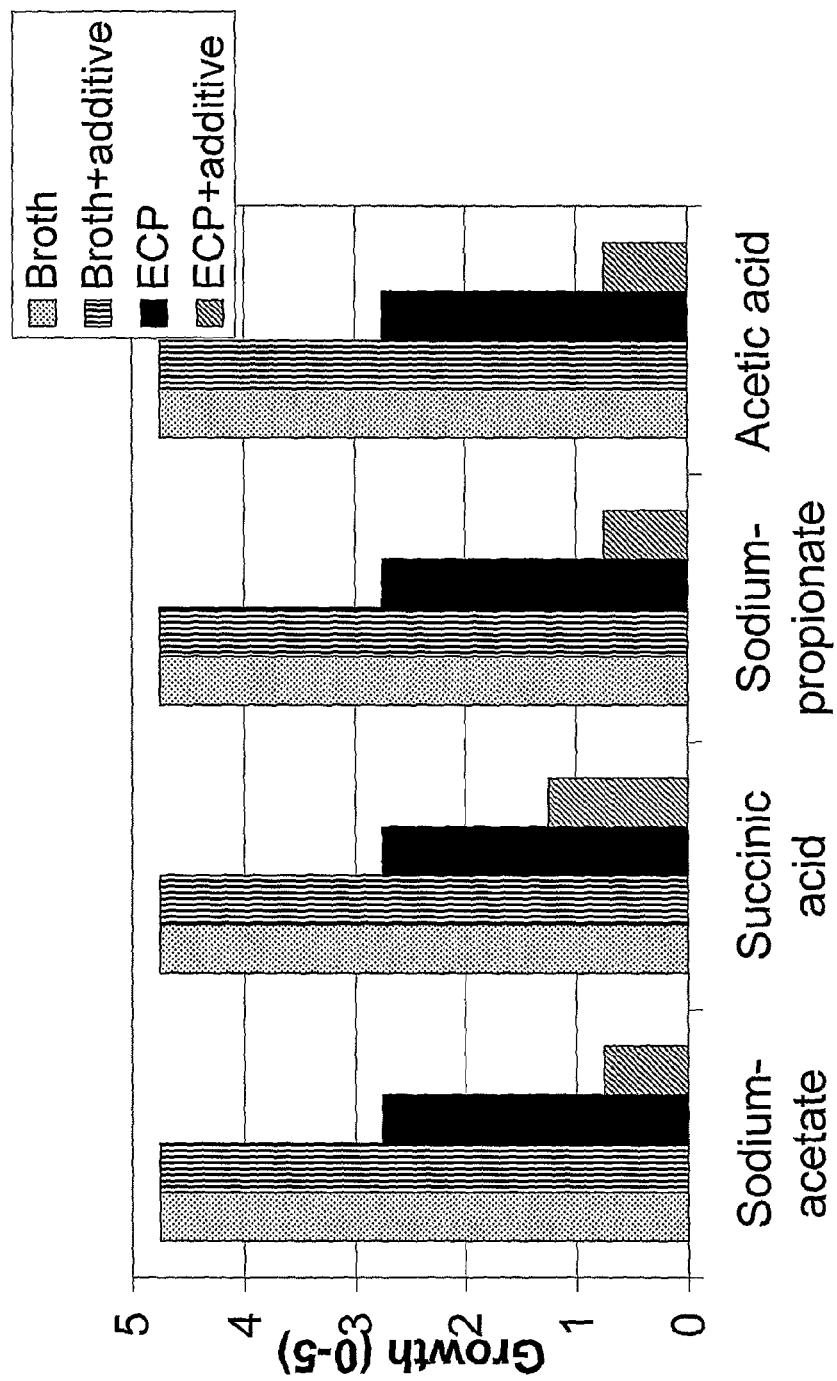
FIG. 2a. shows the growth of *E. coli* in extracellular product of LB 931 with addition (50 mM) of different acids/salts.

As can be seen in FIG. 2A none of the tested additives alone proved to have an effect on the growth of *E. coli*. The extracellular product of LB 931 was effective in the inhibition of *E. coli*. This effect was surprisingly enhanced by the addition of the additives to the extracellular products of LB 931. For all additives in combination with the extracellular product of LB931, a very good growth inhibiting effect was achieved.

Figure 2B:
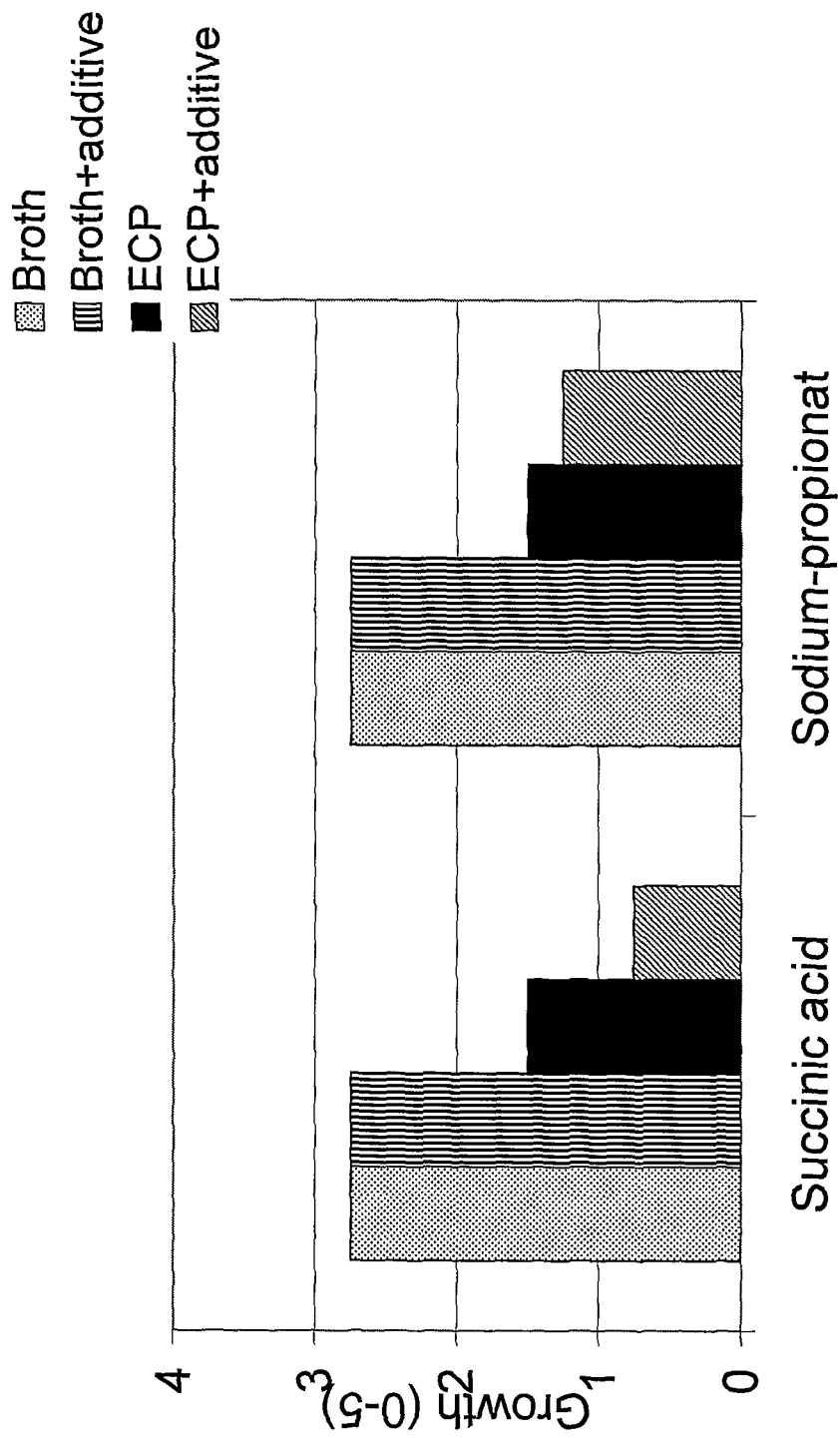
FIG. 2b. shows the growth of *S. Saprofyticus* in extracellular product of LB 931 with addition (50 mM) of different acids/salts.

As can be seen in FIG. 2B none of the tested additives alone proved to have an effect on the growth of *Staphylococcus saprophyticus*. The extracellular product of LB 931 was effective in the inhibition of *Staphylococcus saprophyticus*. This effect was surprisingly enhanced by the addition of the additives to the extracellular products of LB 931. For all additives in combination with the extracellular product of LB 931, a very good growth inhibiting effect was achieved.

Test 3

The purpose of this test was to evaluate the enhanced inhibition of *Candida albicans* when extracellular product of the *Lactobacillus fermentum* Ess-1 was combined with the additives ascorbic acid or propionic acid.

Method

Ess-1 was grown to stationary phase in dMRSs broth (MRS broth without addition of sodium acetate). The bacterial culture was centrifuged to pellet the cells and sterile filtered using a 0.22 µm filter (Millipore filter, Bedford, USA) whereupon the supernatant comprising the extracellular product was obtained. Propionic acid and ascorbic acid were added to a final concentration of 50 mM to tubes containing the extracellular product. The filtrate was pH adjusted to the pKa-value for respective acid (4.2 for ascorbic acid and 4.87 for propionic acid) and 200 µl were transferred to wells of a 96-wells micro titre plate. *C. albicans* was added to a final concentration of $\sim 5 \times 10^4$ CFU $ml^{-1}$ to each wells. The plates were incubated for 20 hours at 37° C. and the growth was evaluated and graduated, by two persons using a template, on a scale from five to zero based on visual observations of turbidity with a calculated mean value being presented. Wells containing strong growth of *Candida* in pure dMRSs-broth was graduated as five, while wells with no visual growth were graduated as zero.

Results

Figure 3A:
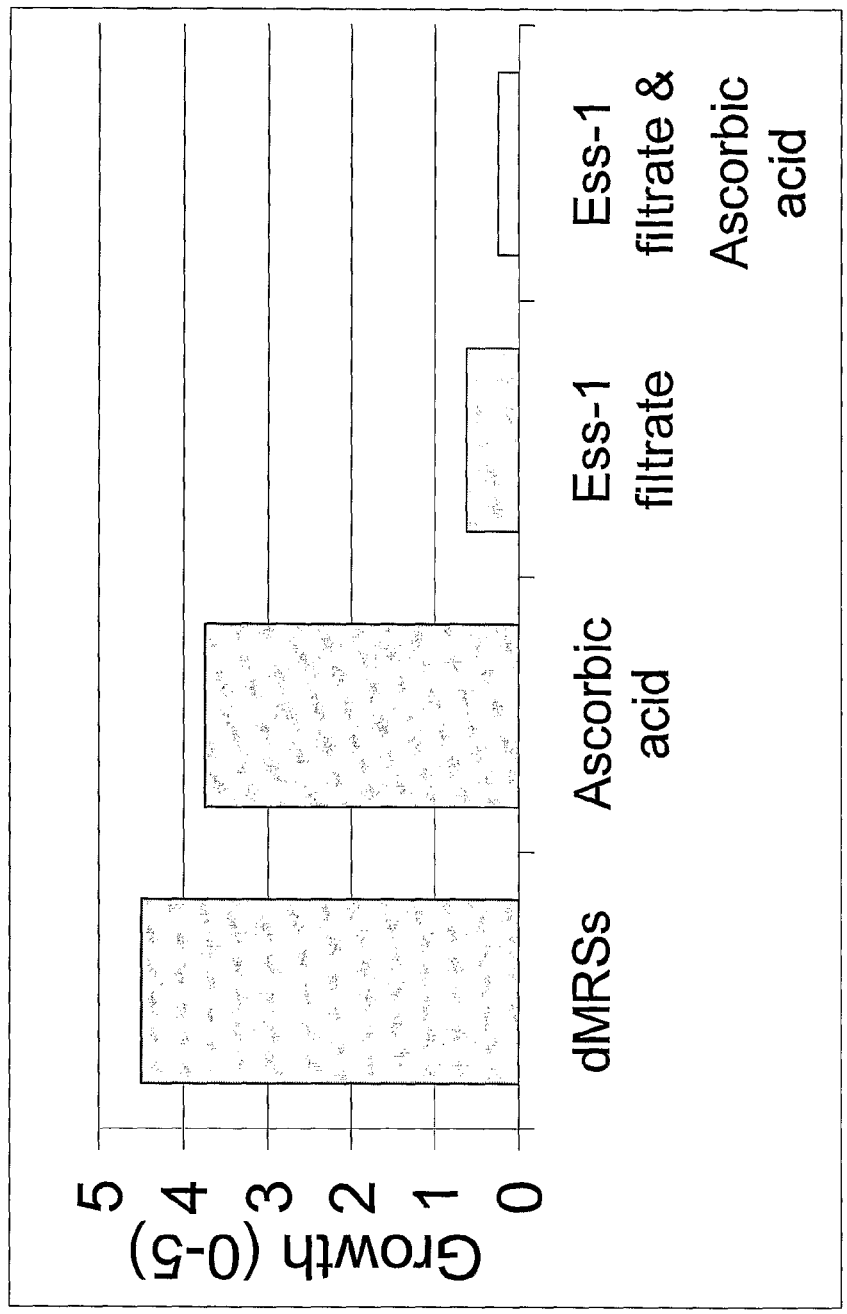
FIG. 3a. shows the growth of *Candida albicans* when extracellular product of the *Lactobacillus fermentum* Ess-1 was combined with the additive ascorbic acid.
Figure 3B:
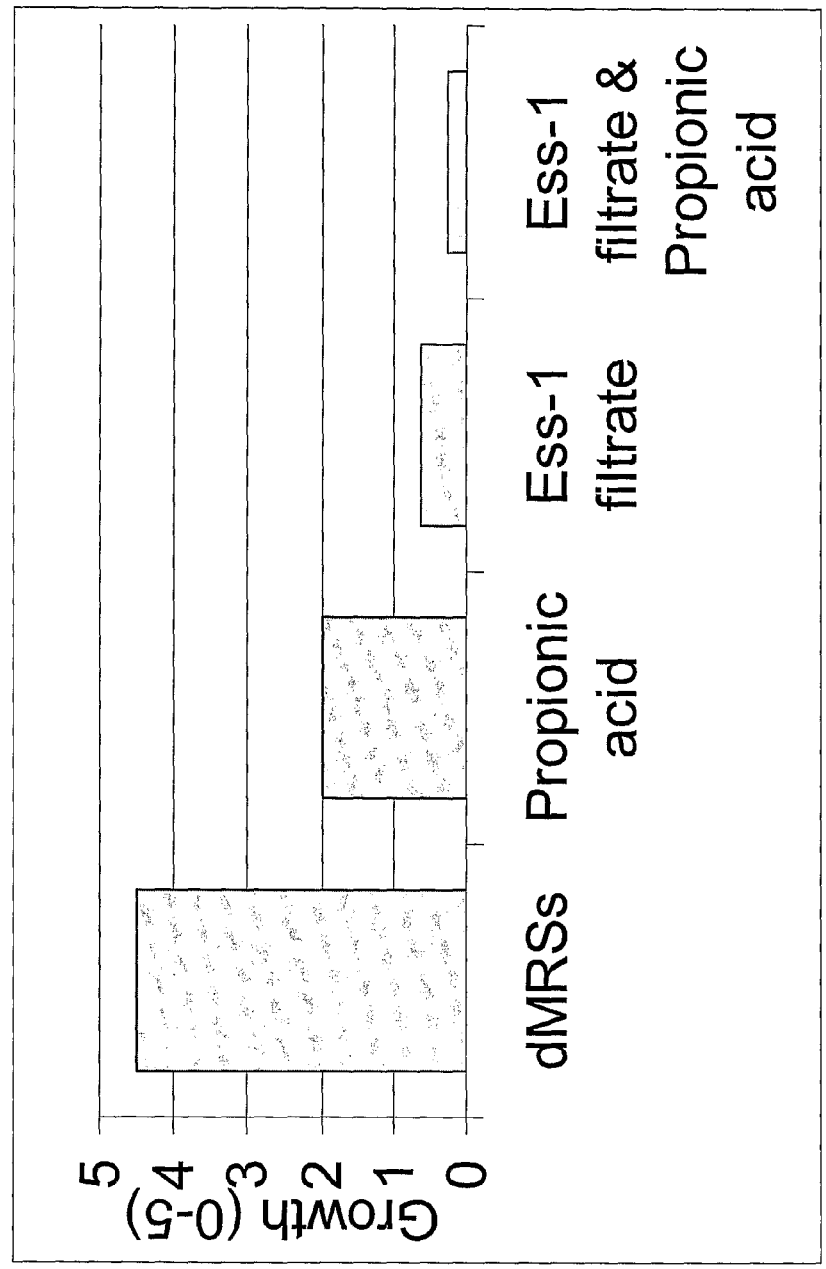
FIG. 3b. shows the growth of *Candida albicans* when extracellular product of the *Lactobacillus fermentum* Ess-1 was combined with the additive propionic acid.

An unexpected increased inhibition was obtained when the supernatant from Ess-1 was combined with either ascorbic acid or propionic acid as can be seen in FIGS. 3A and 3B respectively.

Test 4

The purpose of this test was to evaluate the enhanced *Candida* inhibition from Na-acetate in combination with growing cells of *Lactobacillus plantarum* LB 931.

Method

Two plates were made with M17 agar and two with MRS agar. MRS medium (developed by De Man, Rogosa and Sharpe), is a growth medium commonly used for *Lactobacillus*. MRS agar from Merck contains 5 g sodium acetate per litre agar. M17 (Oxoid) is a similar commercial substrate for *Lactobacillus* but without the addition of sodium acetate. The agars were prepared as described on the packages.

*Lactobacillus plantarum* LB931 was cultivated in MRS broth in 37° C. with 5% $CO_2$ for 24 hours. *Candida albicans* 702 was cultivated in M17 broth at 37° C. for 24 hours.

Holes (Ø10 mm) were punched in the plates and filled with 250 µl plugs of agar mixtures containing $\sim 10^7$ LB 931 in MRS agar). The plates were left for 30 minutes and then incubated 24 hours at 37° C. with 5% $CO_2$. Overnight culture of *C. albicans* in M17 broth was diluted 10 times and 100 µl was spread on the surface of each plate. The plates were then incubated for 24 hours at 37° C. As controls, holes (Ø10 mm) were filled with only MRS agar.

The plates were evaluated in respect to *Candida* growth inhibition. Zones around the plugs with no growth of *Candida* were measured (Ø mm).

Results

The sizes of the zones can be seen in Table 1

TABLE 1

| Agar in the Petri dish | Plug with only agar (Ø mm) | Plug with LB931 (Ø mm) |
| --- | --- | --- |
| MRS agar | 0 | 18.8 |
| M17 agar | 0 | 0 |
| MRS agar | 0 | 18.1 |
| M17 agar | 0 | 0 |

LB 931 grew well in all plugs where LB 931 had been inoculated. There were no zones without growth of *Candida* on the plates with M17 agar. On the MRS agar plates there were clear zones around the LB 931 plugs but no zones around the plugs with only agar.

LB 931 was applied in quite low amounts to the plates, which may explain why substantially no inhibition of *Candida* was seen on the M17 agar plates. This however indicates the efficient inhibition of *Candida* due to the synergistic effect of LB 931 and the additive, in this case sodium acetate comprised in the MRS medium.

EXAMPLES

The following examples related to this invention are illustrative and should not, of course, be construed as specifically limiting the invention.

Example 1

Isolation and Typing of Ess-1

The initial purpose of this study is to isolate and type a *Lactobacillus* strain that inhibit the growth of *Candida albicans* and *Candida glabrata* to a large extent compared to other *Lactobacillus* strains.

Method
Yeast Strains

Clinical isolates of *Candida albicans* and *Candida glabrata* were used as test strains. These were isolated from the vagina of women with vaginal candidiasis and from healthy females.

Screening I.

About 140 *Lactobacillus* strains, originating from human skin, throat, teeth, baby faeces, vegetables and seeds were cultured in MRS broth and stamped onto MRS agar plates. The agar plates were incubated under anaerobic conditions at 37° C. Additionally, SAB (Sabouraud) agar (LAB M, Bury, UK) was poured onto the MRS agar and was allowed to congeal. *C. albicans* culture was seeded onto the agar and the plates were incubated aerobically at 37° C. A visual evaluation of the inhibition was done. Strains inhibiting *C. albicans* equally or to a greater extent than the reference strain *Lactobacillus plantarum* LB931 were selected for further screening (screening II).

Screening II.

Suspensions of lactobacilli grown in dMRSs broth (MRS broth without addition of sodium acetate) were centrifuged and sterile filtered. The filtrate is henceforth called *Lactobacillus* Cell-free Filtrate, LCF. A specified volume was transferred to wells of a micro titre plate and was let to air dry and thereafter resuspended in sterile distilled water to a concentration three times higher and transferred to 96-wells micro titre plates. *Candida* was added to all vials (three isolates of *C. albicans* and *C. glabrata*, respectively, were used). The inhibition was evaluated by visual observation of turbidity and graduated by two persons using a template on a scale from five to zero. The wells containing strong growth of *Candida* sp. in pure dMRSs-broth was graduated as five, while wells with no visual growth were graduated as zero.

API Typing and Genetic Typing

Identification to the species level was done using the API 50 CHL system (bioMérieux, France), following the manufacturer's instructions. Data from the fermentation tests were analysed using API Lab Plus software. Genetic typing was done by DSMZ (Deutsche Sammlung von Microorganismen und Zellkulturen GmbH) by partial sequence analysis of the 16S rRNA.

Results

All strains were evaluated according to the growth inhibition capacity against *C. albicans* in screening I. 23 *Lactobacillus* strains with results comparable or exceeding the one for LB931 were selected for screening II. Out of those 23 *Lactobacillus* strains, three were reference strains and a majority of the strains had been isolated from the oral tract.

Ess-1 proved to have a comprehensive capacity to inhibit growth of *Candida*. No one of the tested *Lactobacillus* strains was similar to the activity of Ess-1 regarding the effect on both *C. albicans* and *C. glabrata*. The carbohydrate fermentation pattern and the genetic typing for Ess-1 showed that it belongs to the *Lactobacillus fermentum* species.

Characterization of Ess-1

16S rDNA from strain Ess-1 (DSM 17851) was analysed by DSMZ (Deutsche Sammlung von Mikroorganismen und Zellkulturen GmbH) by direct sequencing of about 450 nucleotides of PCR-amplified 16S rDNA. Genomic DNA extraction, PCR mediated amplification of the 16S rDNA and purification of the PCR product was carried our as previously described (Rainey, F. A. et al. Int. J. Sys. Bacteriol. 1996(46): 1088-1092). Purified PCR products were sequenced using the CEQ™DTCS-Quickstart Kit (Beckamn Coulter) following the manufacturers instructions. Sequence reaction products were electrophoresed using the CEQ™8000 Genetic Analysis System.

The resulting sequence data was put into the alignment editor ae2 (Maidak, B. L. et al. Nucl. Acids Res. 1999(27): 171-173), aligned manually and compared with representative 16S rRNA gene sequences of organism belonging to the Firmicutes (Maidak, B. L. et al.). For comparison 16S rRNA sequences were obtained from the EMBL data base or RDP (Maidak, B. L. et al.).

As a result of this analysis the following table 2 lists those organisms, whose 16S rRNA gene sequences show the highest similarity values compared to the 16S rDNA sequence of Ess-1.

TABLE 2

| Strain | % 16S rRNA gene sequence similarity to Ess-1 |
|---|---|
| *Lactobacillus fermentum* ATCC 14931 | 99.3 |
| *Lactobacillus fermentum* KRM | 99.0 |
| *Lactobacillus malefermentans* DSM 5705 | 85.5 |
| *Lactobacillus rossiae* ATCC BAA-822 | 88.9 |
| *Lactobacillus suebicus* DSM 5007 | 86.9 |
| *Lactobacillus vaccinostercus* DSM 20634 | 87.2 |

The partial 16S rDNA gene sequence of strain Ess-1 shows highest similarity to *Lactobacillus fermentum*. Consequently strain Ess-1 may represent a strain of *Lactobacillus fermentum*, but may as well represent a new species within the genus *Lactobacillus*.

Example 2

Production of Probiotic *Lactobacillus*

In laboratory scale: a sterile vessel with ex. MRS broth is inoculated with a pure inoculate of the desired *lactobacillus* strain. Broth with bacteria is incubated over night in 37 C.° and preferably with an atmosphere of 5% $CO_2$. Cells may then be washed using centrifugation and sterile saline. Protective sugar, starch or proteins may be added and the cell-mass freeze-dried and milled.

In production scale, the working sead lot is fermented in different steps up to production scale. The production is controlled and optimised for the specific strain to be produced. After fermentation the culture is washed and/or only concentrated using cross-flow microfiltration or centrifugation. Protective substances according to the above are added and the cells can be freeze-dried and milled or spray-dried.

Example 3

Production of Extracellular Product from e.g. *Lactobacillus*

In laboratory scale the overnight culture of the probiotic strain is produced as in Example 2. After filtration or centrifugation the supernatant is collected. The supernatant may be concentrated by evaporation or completely dried for ex. convective drying in dry air, freeze, drying or spray-drying.

In production scale the bacterial culture is fermented in accordance with Example 2. The extracellular product is obtained as a filtrate using cross-flow micro filtration or a supernatant using centrifugation. Also in this case it may be further concentrated using evaporation or completely dry using for eg. spray-drying.

Example 4

Formulations

Anti Candida Panty Liner

The product is based on a standard marketed panty liner, such as Libresse® extra liners (sold by SCA Hygiene Products AB), to which the extracellular product of Ess-1 in combination with an additive, is added according to the following: 10 ml of the extracellular product of Ess-1 is evaporated to 1 ml to which 3.7 mg of propionic acid is added. The extracellular product with propionic acid is printed on the surface of the panty liner which is dried before packaging.

Light Incontinence Pad with Reduced Bacterial Growth and Odour Control

The product is based on a standard marketed light incontinence pad, such as Tena® Lady Normal (sold by SCA Hygiene Products AB), to which the extracellular products of LB931 is added according to the following: 100 ml of the extracellular product of LB931 are mixed with 1 g of citric acid. The mixture is evaporated and dried and thereafter the powder is homogenously mixed in the absorbent core of the pad.

Light Liner for Improved Genital Hygiene

The product is based on a standard marketed panty liner, such as Libresse® light liners (sold by SCA Hygiene products AB), to which the extracellular products of both Ess-1 and LB931 are added according to the following: 5 ml of the extracellular product of Ess-1 and 5 ml of the extracellular product of LB931 are mixed and evaporated to 1 ml, to which 4.1 mg of sodium acetate are added. The mixture is evaporated and dried and the powder is mixed with 0.1 g of silicone wax and finally printed in the centre of the top sheet of the liner.

It should be noted that even if all three examples on formulations only comprise *Lactobacillus plantarum* LB 931 and/or *Lactobacillus fermentum* Ess-1 as probiotic bacteria, all probiotic bacteria suitable for the present invention as previously described may as well be used.

The invention claimed is:

1. A sanitary article comprising a top sheet, said sanitary article comprising, prior to use of the sanitary article: a microbe-inhibiting composition, said microbe-inhibiting composition comprising:
   an extracellular product of at least one probiotic bacterium, or at least one probiotic bacterium, and
   at least one additive in the form of an organic acid, having a pKa value not exceeding 5.5, or a salt of the organic acid,
   wherein, when the microbe-inhibiting composition comprises the extracellular product, the additive is present in a concentration of 5-100 mM, and when the microbe-inhibiting composition comprises the probiotic bacteria excluding the extracellular product thereof, the additive is present in an amount of 0.15 mg-2.6 g per the sanitary article.

2. The sanitary article according to claim 1, wherein said pKa value does not exceed 5.

3. The sanitary article according to claim 1, wherein said extracellular product is in the form of a supernatant, obtained by centrifugation or filtration of a culture of a probiotic bacterium.

4. The sanitary article according to claim 1, wherein said microbe-inhibiting composition comprises at least one probiotic bacterium and at least one of said additives.

5. The sanitary article according to claim 1, wherein said microbe-inhibiting composition comprises at least one probiotic bacterium, an extracellular product of at least one probiotic bacterium and at least one of said additives.

6. The sanitary article according to claim 1, wherein said microbe-inhibiting composition is substantially free from probiotic bacteria.

7. The sanitary article according to claim 1, wherein said probiotic bacterium is a lactic acid producing bacterium.

8. The sanitary article according to claim 7, wherein said lactic acid producing bacterium is *Lactobacillus plantarum* LB 931 or *Lactobacillus fermentum* Ess-1 or a combination thereof.

9. The sanitary article according to claim 1, wherein said additive is selected from the group consisting of acetic acid, propionic acid, lactic acid, ascorbic acid, phenylalanine, citric acid, butyric acid, valeric acid, capronic acid, succinic acid and salts thereof.

10. The sanitary article according to claim 9, wherein said additive is a sodium salt of acetic acid, propionic acid, lactic acid, ascorbic acid, phenylalanine, citric acid, butyric acid, valeric acid, capronic acid, or succinic acid.

11. The sanitary article comprising a microbe-inhibiting composition according to claim 1, wherein the microbe-inhibiting composition is located on the top sheet.

12. A kit comprising, prior to use of the kit:
    a microbe-inhibiting composition comprising:
       an extracellular product of at least one probiotic bacterium, or at least one probiotic bacterium, and
       at least one additive in the form of an organic acid, having a pKa value not exceeding 5.5, or a salt of the organic acid, and
    a sanitary article,
    wherein when the microbe-inhibiting composition comprises the extracellular product, the additive is present in a concentration of 5-100 mM, and when the microbe-inhibiting composition comprises the probiotic bacteria excluding the extracellular product thereof, the additive is present in an amount of 0.15 mg-2.6 g per the sanitary article.

13. The kit according to claim 12, wherein said microbe-inhibiting composition is provided in an ampoule, a bottle, a tube, a roll-on device, as a stick or a spray.

14. A method of preparing a sanitary article according to claim 1 comprising applying said microbe-inhibiting composition to said sanitary article.

15. The sanitary article according to claim 6, wherein the probiotic bacteria are present in an amount not higher than 10 CFU/ml.

16. The sanitary article according to claim 9, wherein said additive is selected from the group consisting of ascorbic acid, acetic acid, propionic acid, succinic acid and salts thereof.

17. The sanitary article according to claim 10, wherein said salt is sodium propionate or sodium acetate.

* * * * *